US010245136B2

United States Patent
Ino et al.

(10) Patent No.: US 10,245,136 B2
(45) Date of Patent: Apr. 2, 2019

(54) CONTAINMENT VESSEL WITH IMPLANT SHEATHING GUIDE

(71) Applicant: BOSTON SCIENTIFIC SCIMED, INC., Maple Grove, MN (US)

(72) Inventors: Takashi H. Ino, San Jose, CA (US); Randy S. Gamarra, Santa Clara, CA (US); Michael P. Calomeni, San Jose, CA (US); Christopher W. Ledesma, Arcadia, CA (US); Mimi Trinh Fitterer, Belmont, CA (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 0 days.

(21) Appl. No.: 15/498,807

(22) Filed: Apr. 27, 2017

(65) Prior Publication Data
US 2017/0325928 A1 Nov. 16, 2017

Related U.S. Application Data

(60) Provisional application No. 62/335,986, filed on May 13, 2016.

(51) Int. Cl.
*A61F 2/24* (2006.01)
*A61F 2/00* (2006.01)
(Continued)

(52) U.S. Cl.
CPC ............ *A61F 2/0095* (2013.01); *A61F 2/243* (2013.01); *A61F 2/2418* (2013.01);
(Continued)

(58) Field of Classification Search
CPC .. A61F 2/00; A61F 2/0095; A61F 2/12; A61F 2/24; A61F 2/2418; A61F 2/243;
(Continued)

(56) References Cited

U.S. PATENT DOCUMENTS 3,334,629 A 5/1967 Cohn
3,409,013 A 11/1968 Berry
(Continued)

FOREIGN PATENT DOCUMENTS

CN 1338951 A 3/2002
EP 0409929 B1 4/1997
(Continued)

OTHER PUBLICATIONS

International Search Report and Written Opinion dated Sep. 20, 2017 for International Application No. PCT/US2017/032050.
(Continued)

*Primary Examiner* — Bryon Gehman
(74) *Attorney, Agent, or Firm* — Seager, Tufte & Wickhem LLP.

(57) ABSTRACT

A containment vessel for storing and rinsing a medical implant coupled to a delivery system having an outer sheath may include a hollow element having a wall, a proximal end, a distal end, and a lumen extending between the proximal end and the distal end, the lumen of the hollow element being configured and adapted to contain a medical implant in a partially-deployed configuration during storage and rinsing of the medical implant and a proximal end cap including a secondary proximal end cap removably secured to the proximal end cap and configured to reversibly seal the proximal end cap to the outer sheath, thereby establishing a closed fluid connection between the lumen of the hollow element and a lumen of the outer sheath. The proximal end cap may include a sheathing guide configured and adapted to direct the medical implant into the lumen of the outer sheath.

20 Claims, 12 Drawing Sheets

(51) Int. Cl.
*A61B 17/34* (2006.01)
*A61F 2/95* (2013.01)

(52) U.S. Cl.
CPC .... *A61F 2/2436* (2013.01); *A61B 2017/3464* (2013.01); *A61F 2/2412* (2013.01); *A61F 2002/9522* (2013.01)

(58) Field of Classification Search
CPC . A61F 2/2436; A61L 2/00; A61L 2/14; A61L 2/26; A61L 27/00; A61L 27/04
USPC .................. 206/363, 364, 438; 623/2.1, 2.11
See application file for complete search history.

(56) References Cited

U.S. PATENT DOCUMENTS

| | | |
|---|---|---|
| 3,540,431 A | 11/1970 | Mobin-Uddin |
| 3,642,004 A | 2/1972 | Osthagen et al. |
| 3,657,744 A | 4/1972 | Ersek |
| 3,671,979 A | 6/1972 | Moulopoulos |
| 3,795,246 A | 3/1974 | Sturgeon |
| 3,834,394 A | 9/1974 | Hunter et al. |
| 3,839,741 A | 10/1974 | Haller |
| 3,868,956 A | 3/1975 | Alfidi et al. |
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,326,306 A | 4/1982 | Poler |
| 4,423,809 A | 1/1984 | Mazzocco |
| 4,425,908 A | 1/1984 | Simon |
| 4,501,030 A | 2/1985 | Lane |
| 4,542,825 A | 9/1985 | Thomas et al. |
| 4,580,568 A | 4/1986 | Gianturco |
| 4,585,453 A | 4/1986 | Martin et al. |
| 4,602,911 A | 7/1986 | Ahmadi et al. |
| 4,610,688 A | 9/1986 | Silvestrini et al. |
| 4,617,932 A | 10/1986 | Kornberg |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | Dipisa, Jr. |
| 4,665,906 A | 5/1987 | Jervis |
| 4,710,192 A | 12/1987 | Liotta et al. |
| 4,733,665 A | 3/1988 | Palmaz |
| 4,755,181 A | 7/1988 | Igoe |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,865,600 A | 9/1989 | Carpentier et al. |
| 4,872,874 A | 10/1989 | Taheri |
| 4,909,252 A | 3/1990 | Goldberger |
| 4,917,102 A | 4/1990 | Miller et al. |
| 4,954,126 A | 9/1990 | Wallsten |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,064,435 A | 11/1991 | Porter |
| 5,161,547 A | 11/1992 | Tower |
| 5,163,953 A | 11/1992 | Vince |
| 5,209,741 A | 5/1993 | Spaeth |
| 5,258,042 A | 11/1993 | Mehta |
| 5,332,402 A | 7/1994 | Teitelbaum |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,403,305 A | 4/1995 | Sauter et al. |
| 5,411,552 A | 5/1995 | Andersen et al. |
| 5,425,762 A | 6/1995 | Muller |
| 5,431,676 A | 7/1995 | Dubrul et al. |
| 5,443,495 A | 8/1995 | Buscemi et al. |
| 5,443,499 A | 8/1995 | Schmitt |
| 5,443,502 A | 8/1995 | Caudillo et al. |
| 5,476,506 A | 12/1995 | Lunn |
| 5,476,510 A | 12/1995 | Eberhardt et al. |
| 5,480,423 A | 1/1996 | Ravenscroft et al. |
| 5,507,767 A | 4/1996 | Maeda et al. |
| 5,534,007 A | 7/1996 | St. Germain et al. |
| 5,545,133 A | 8/1996 | Burns et al. |
| 5,545,211 A | 8/1996 | An et al. |
| 5,549,665 A | 8/1996 | Vesely et al. |
| 5,554,127 A | 9/1996 | Crouther et al. |
| 5,554,185 A | 9/1996 | Block et al. |
| 5,560,487 A | 10/1996 | Starr |
| 5,571,215 A | 11/1996 | Sterman et al. |
| 5,575,818 A | 11/1996 | Pinchuk |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,695,498 A | 12/1997 | Tower |
| 5,713,953 A | 2/1998 | Vallana et al. |
| 5,716,370 A | 2/1998 | Williamson, IV et al. |
| 5,720,391 A | 2/1998 | Dohm et al. |
| 5,733,325 A | 3/1998 | Robinson et al. |
| 5,735,842 A | 4/1998 | Krueger et al. |
| 5,769,812 A | 6/1998 | Stevens et al. |
| 5,800,456 A | 9/1998 | Maeda et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,843,158 A | 12/1998 | Lenker et al. |
| 5,855,597 A | 1/1999 | Jayaraman |
| 5,855,601 A | 1/1999 | Bessler et al. |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,907,893 A | 6/1999 | Ladno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,093,203 A | 7/2000 | Uflacker |
| 6,123,723 A | 9/2000 | Konya et al. |
| 6,142,987 A | 11/2000 | Tsugita |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,171,327 B1 | 1/2001 | Daniel et al. |
| 6,179,859 B1 | 1/2001 | Bates et al. |
| 6,187,016 B1 | 2/2001 | Hedges et al. |
| 6,197,053 B1 | 3/2001 | Cosgrove et al. |

(56) References Cited

U.S. PATENT DOCUMENTS

| | | |
|---|---|---|
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,416,510 B1 | 7/2002 | Altman et al. |
| 6,416,547 B1 | 7/2002 | Erickson et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,485,501 B1 | 11/2002 | Green |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford, III et al. |
| 6,712,843 B2 | 3/2004 | Elliott |
| 6,714,842 B1 | 3/2004 | Ito |
| 6,719,789 B2 | 4/2004 | Cox |
| 6,723,122 B2 | 4/2004 | Yang et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat et al. |
| 6,776,791 B1 | 8/2004 | Stallings et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,814,746 B2 | 11/2004 | Thompson et al. |
| 6,821,297 B2 | 11/2004 | Snyders |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,953,332 B1 | 10/2005 | Kurk et al. |
| 6,964,673 B2 | 11/2005 | Tsugita et al. |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,122,020 B2 | 10/2006 | Mogul |
| 7,166,097 B2 | 1/2007 | Barbut |
| 7,175,653 B2 | 2/2007 | Gaber |
| 7,175,654 B2 | 2/2007 | Bonsignore et al. |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,318,278 B2 | 1/2008 | Zhang et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,389,874 B2 | 6/2008 | Quest et al. |
| 7,445,631 B2 | 11/2008 | Salahieh et al. |
| 7,632,298 B2 | 12/2009 | Hijlkema et al. |
| 7,699,168 B2 | 4/2010 | Ryan et al. |
| 7,712,606 B2 | 5/2010 | Salahieh et al. |
| 7,722,666 B2 | 5/2010 | Lafontaine |
| 7,748,389 B2 | 7/2010 | Salahieh et al. |
| 7,824,442 B2 | 11/2010 | Salahieh et al. |
| 7,824,443 B2 | 11/2010 | Salahieh et al. |
| 7,959,666 B2 | 6/2011 | Salahieh et al. |
| 7,959,672 B2 | 6/2011 | Salahieh et al. |
| 7,967,138 B2 | 6/2011 | Ryan et al. |
| 7,988,724 B2 | 8/2011 | Salahieh et al. |

(56) References Cited

U.S. PATENT DOCUMENTS

| | | |
|---|---|---|
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,182,528 B2 | 5/2012 | Salahieh et al. |
| 8,231,670 B2 | 7/2012 | Salahieh et al. |
| 8,246,678 B2 | 8/2012 | Salahieh et al. |
| 8,252,052 B2 | 8/2012 | Salahieh et al. |
| 8,287,584 B2 | 10/2012 | Salahieh et al. |
| 8,328,868 B2 | 12/2012 | Paul et al. |
| 8,343,213 B2 | 1/2013 | Salahieh et al. |
| 8,851,286 B2 * | 10/2014 | Chang ............... A61F 2/2436 |
| | | 206/438 |
| 8,893,370 B2 | 11/2014 | Hillukka et al. |
| 8,951,299 B2 | 2/2015 | Paul et al. |
| 8,985,331 B2 * | 3/2015 | Guenter ............... A61C 8/0087 |
| | | 206/438 |
| 9,066,785 B2 | 6/2015 | Tran et al. |
| 9,155,619 B2 | 10/2015 | Liu et al. |
| 9,168,135 B2 | 10/2015 | Dale et al. |
| 9,192,496 B2 | 11/2015 | Robinson |
| 9,707,077 B2 * | 7/2017 | Chang ............... A61L 2/26 |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0032481 A1 | 3/2002 | Gabbay |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0177766 A1 | 11/2002 | Mogul |
| 2002/0188341 A1 | 12/2002 | Elliott |
| 2002/0188344 A1 | 12/2002 | Bolea et al. |
| 2003/0023303 A1 | 1/2003 | Palmaz et al. |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0045928 A1 | 3/2003 | Yang et al. |
| 2003/0050694 A1 | 3/2003 | Yang et al. |
| 2003/0055495 A1 | 3/2003 | Pease et al. |
| 2003/0060844 A1 | 3/2003 | Borillo et al. |
| 2003/0070944 A1 | 4/2003 | Nigam |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149476 A1 | 8/2003 | Damm et al. |
| 2003/0149478 A1 | 8/2003 | Figulla et al. |
| 2003/0168370 A1 | 9/2003 | Merboth et al. |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0098022 A1 | 5/2004 | Barone |
| 2004/0098099 A1 | 5/2004 | McCullagh et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0181140 A1 | 9/2004 | Falwell et al. |
| 2004/0186563 A1 | 9/2004 | Lobbi |
| 2004/0204755 A1 | 10/2004 | Robin |
| 2004/0215331 A1 | 10/2004 | Chew et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0254636 A1 | 12/2004 | Flagle et al. |
| 2005/0033402 A1 | 2/2005 | Cully et al. |
| 2005/0043711 A1 | 2/2005 | Corcoran et al. |
| 2005/0075662 A1 | 4/2005 | Pedersen et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | Wasdyke |
| 2005/0113910 A1 | 5/2005 | Paniagua et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2005/0165352 A1 | 7/2005 | Henry et al. |
| 2005/0165477 A1 | 7/2005 | Anduiza et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |

(56) References Cited

U.S. PATENT DOCUMENTS

| | | |
|---|---|---|
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0015177 A1 | 1/2006 | Quest et al. |
| 2006/0058872 A1 | 3/2006 | Salahieh et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0260967 A1 | 11/2006 | Clarke et al. |
| 2006/0271166 A1 | 11/2006 | Thill et al. |
| 2006/0287668 A1 | 12/2006 | Fawzi et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0203503 A1 | 8/2007 | Salahieh et al. |
| 2007/0244552 A1 | 10/2007 | Salahieh et al. |
| 2008/0010947 A1 | 1/2008 | Huang et al. |
| 2008/0125859 A1 | 5/2008 | Salahieh et al. |
| 2008/0234814 A1 | 9/2008 | Salahieh et al. |
| 2008/0288054 A1 | 11/2008 | Pulnev et al. |
| 2009/0008279 A1 | 1/2009 | Tanghoej |
| 2009/0054969 A1 | 2/2009 | Salahieh et al. |
| 2009/0076598 A1 | 3/2009 | Salahieh et al. |
| 2009/0222076 A1 | 9/2009 | Figulla et al. |
| 2009/0264997 A1 | 10/2009 | Salahieh et al. |
| 2010/0121434 A1 | 5/2010 | Paul et al. |
| 2010/0219092 A1 | 9/2010 | Salahieh et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0252470 A1 | 10/2010 | Ryan et al. |
| 2010/0256749 A1 | 10/2010 | Tran et al. |
| 2010/0280495 A1 | 11/2010 | Paul et al. |
| 2011/0257735 A1 | 10/2011 | Salahieh et al. |
| 2011/0276129 A1 | 11/2011 | Salahieh et al. |
| 2012/0016469 A1 | 1/2012 | Salahieh et al. |
| 2012/0016471 A1 | 1/2012 | Salahieh et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0116351 A1 | 5/2012 | Chomas et al. |
| 2012/0132547 A1 | 5/2012 | Salahieh et al. |
| 2012/0290079 A1 | 11/2012 | Murad et al. |
| 2012/0330409 A1 | 12/2012 | Haug et al. |
| 2013/0118949 A1 | 5/2013 | Chang et al. |
| 2014/0042050 A1* | 2/2014 | Richart ............... A61B 19/026 206/438 |
| 2014/0277403 A1 | 9/2014 | Peter |
| 2015/0297381 A1 | 10/2015 | Essinger et al. |
| 2016/0302906 A1* | 10/2016 | Lam .................... A01N 1/0273 |

FOREIGN PATENT DOCUMENTS

| | | | |
|---|---|---|---|
| EP | 0819013 | A1 | 1/1998 |
| EP | 0937439 | A2 | 8/1999 |
| EP | 1000590 | A1 | 5/2000 |
| EP | 1057459 | A1 | 12/2000 |
| EP | 1057460 | A1 | 12/2000 |
| EP | 1059894 | | 12/2000 |
| EP | 1078610 | A2 | 2/2001 |
| EP | 1340473 | A2 | 9/2003 |
| EP | 1356793 | A2 | 10/2003 |
| EP | 1042045 | B1 | 5/2004 |
| EP | 1430853 | A2 | 6/2004 |
| EP | 1469797 | A1 | 10/2004 |
| EP | 1229864 | B1 | 4/2005 |
| EP | 1576937 | A2 | 9/2005 |
| EP | 1582178 | A2 | 10/2005 |
| EP | 1582179 | A2 | 10/2005 |
| EP | 1600121 | A1 | 11/2005 |
| EP | 1156757 | B1 | 12/2005 |
| EP | 1616531 | A2 | 1/2006 |
| WO | 9315693 | A1 | 8/1993 |
| WO | 9504556 | A2 | 2/1995 |
| WO | 9529640 | A1 | 11/1995 |
| WO | 9614032 | A1 | 5/1996 |
| WO | 9624306 | A1 | 8/1996 |
| WO | 9836790 | A1 | 8/1998 |
| WO | 9850103 | A1 | 11/1998 |
| WO | 9857599 | A2 | 12/1998 |
| WO | 9944542 | A2 | 9/1999 |
| WO | 0009059 | A2 | 2/2000 |
| WO | 0044308 | A2 | 8/2000 |
| WO | 0044313 | A1 | 8/2000 |
| WO | 0049970 | A1 | 8/2000 |
| WO | 0067661 | A2 | 11/2000 |
| WO | 0105331 | A1 | 1/2001 |
| WO | 0108596 | A1 | 2/2001 |
| WO | 0110320 | A1 | 2/2001 |
| WO | 0110343 | A1 | 2/2001 |
| WO | 0135870 | A1 | 5/2001 |
| WO | 0164137 | A1 | 9/2001 |
| WO | 0236048 | A1 | 5/2002 |
| WO | 0241789 | A2 | 5/2002 |
| WO | 02100297 | A2 | 12/2002 |
| WO | 03003943 | A2 | 1/2003 |
| WO | 03003949 | A2 | 1/2003 |
| WO | 03011195 | A2 | 2/2003 |
| WO | 03030776 | A2 | 4/2003 |
| WO | 03015851 | B1 | 11/2003 |
| WO | 03094797 | A1 | 11/2003 |
| WO | 2004014256 | A1 | 2/2004 |
| WO | 2004019811 | A2 | 3/2004 |
| WO | 2004023980 | A2 | 3/2004 |
| WO | 2004026117 | A2 | 4/2004 |
| WO | 2004041126 | A1 | 5/2004 |
| WO | 2004047681 | A1 | 6/2004 |
| WO | 2004066876 | A1 | 8/2004 |
| WO | 2004082536 | A1 | 9/2004 |
| WO | 2005084595 | A1 | 9/2005 |
| WO | 2005087140 | A1 | 9/2005 |
| WO | 2005120395 | A2 | 12/2005 |
| WO | 2014141209 | A1 | 9/2014 |
| WO | 2015062534 | A1 | 5/2015 |

OTHER PUBLICATIONS

Andersen et al., "Transluminal implantation of artificial heart valves. Description of a new expandable aortic valve and initial results with implantation by catheter technique in closed chest pigs." Euro. Heart J., 13:704-708, May 1992.

Atwood et al., "Insertion of Heart Valves by Catheterization." Project Supervised by Prof. S. Muftu of Northeastern University 2001-2002: 36-40, May 30, 2002.

Bodnar et al., "Replacement Cardiac Valves R Chapter 13: Extinct Cardiac Valve Prostheses." Pergamon Publishing Corporation. New York, 307-322, 1991.

Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.

Boudjemline et al., "Percutaneous Implantation of a Valve in the Descending Aorta in Lambs." Euro. Heart J., 23: 1045-1049, Jul. 2002.

(56) References Cited

OTHER PUBLICATIONS

Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Ferrari et al., "Percutaneous Transvascular Aortic Valve Replacement with Self-Expanding Stent-Valve Device." Poster from the presentation given at SMIT 2000, 12th International Conference. Sep. 5, 2000.
Hijazi, "Transcatheter Valve Replacement: A New Era of Percutaneous Cardiac Intervention Begins." J. of Am. College of Cardio., 43(6): 1088-1089, Mar. 17, 2004.
Huber et al., "Do Valved Stents Compromise Coronary Flow?" European Journal of Cardio-thoracic Surgery, vol. 25: 754-759, Jan. 23, 2004.
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Moulopoulos et al., "Catheter-Mounted Aortic Valves." Annals of Thoracic Surg., 11(5): 423-430, May 1971.
Paniagua et al., "Heart Watch." Texas Heart Institute. Edition: 8 pages, Spring, 2004.
Paniagua et al., "Percutaneous Heart Valve in the Chronic in Vitro Testing Model." Circulation, 106: e51-e52, Sep. 17, 2002.
Pavcnik et al., "Percutaneous Bioprosthetic Venous Valve: A Long-term Study in Sheep." J. of Vascular Surg., 35(3): 598-603, Mar. 2002.
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Sochman et al., "Percutaneous Transcatheter Aortic Disc Valve Prosthesis Implantation: A Feasibility Study." Cardiovasc. Intervent. Radiol., 23: 384-388, Sep. 2000.
Stuart, "In Heart Valves, A Brave, New Non-Surgical World." Start-Up. 9-17, Feb. 2004.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
Zhou et al, "Self-expandable Valved Stent of Large Size: Off-Bypass Implantation in Pulmonary Position." Eur. J. Cardiothorac, 24: 212-216, Aug. 2003.
U.S. Pat. No. 8,062,356, Nov. 2011, Salahieh et al. (withdrawn).
U.S. Pat. No. 8,062,357, Nov. 2011, Salahieh et al. (withdrawn).
U.S. Pat. No. 8,075,614, Dec. 2011, Salahieh et al. (withdrawn).
U.S. Pat. No. 8,133,271, Mar. 2012, Salahieh et al. (withdrawn).
U.S. Pat. No. 8,211,170, Jul. 2012, Paul et al. (withdrawn).

\* cited by examiner

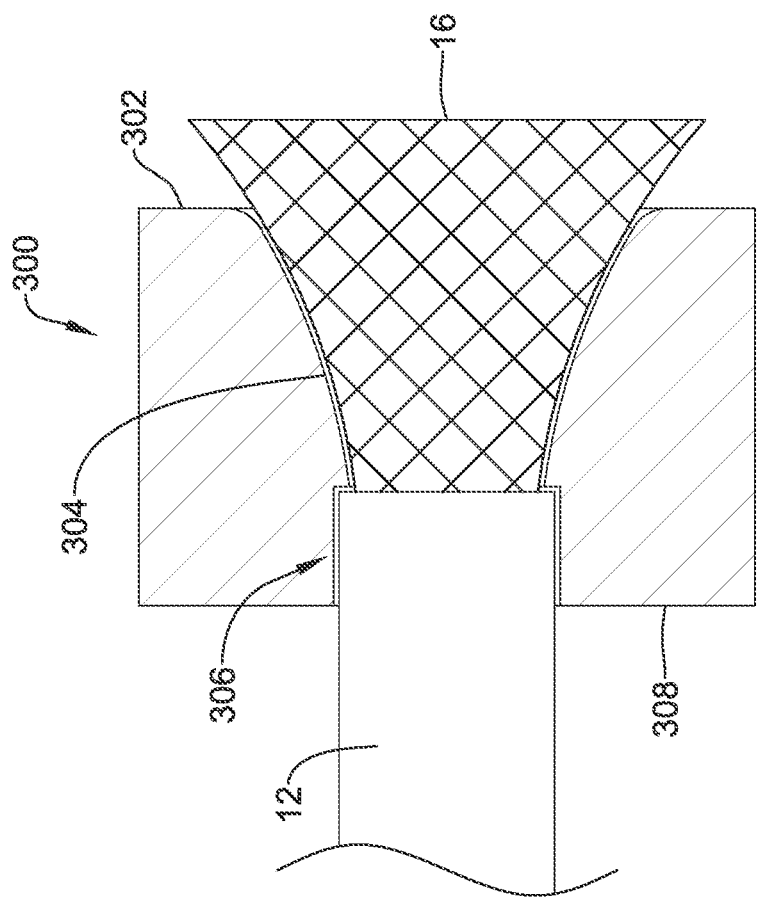

CONTAINMENT VESSEL WITH IMPLANT SHEATHING GUIDE

RELATED APPLICATIONS

This application claims priority to U.S. Provisional Application No. 62/335,986, filed May 13, 2016.

TECHNICAL FIELD

The present disclosure pertains to medical devices, and methods for manufacturing and/or using medical devices. More particularly, the present disclosure pertains to configurations of a containment vessel for storing and sterilizing a medical implant such as a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a containment vessel for storing and sterilizing a medical implant coupled to a delivery system having an outer sheath, the containment vessel may include a hollow element having a wall, a proximal end, a distal end, and a lumen extending between the proximal end and the distal end, the lumen of the hollow element being configured and adapted to contain a medical implant in a partially-deployed configuration during storage and sterilizing of the medical implant and a proximal end cap including a secondary proximal end cap removably secured to the proximal end cap and configured to reversibly seal the proximal end cap to the outer sheath, thereby establishing a closed fluid connection between the lumen of the hollow element and a lumen of the outer sheath. The proximal end cap may include a sheathing guide configured and adapted to direct the medical implant into the lumen of the outer sheath.

In addition or alternatively, and in a second aspect, the medical implant is stored within the lumen of the hollow element in a wet condition.

In addition or alternatively, and in a third aspect, the containment vessel for the medical implant includes a distal end cap having an outlet configured to selectively release storage fluid from within the lumen of the hollow element.

In addition or alternatively, and in a fourth aspect, the storage fluid includes one or more biocidal fluids.

In addition or alternatively, and in a fifth aspect, the distal end cap includes an outlet configured to selectively release rinsing fluid from within the lumen of the hollow element.

In addition or alternatively, and in a sixth aspect, the sheathing guide is integrally formed with the proximal end cap.

In addition or alternatively, and in a seventh aspect, the containment vessel for the medical implant includes a radiopaque sleeve disposed about the lumen of the hollow element.

In addition or alternatively, and in an eighth aspect, the radiopaque sleeve is disposed about the wall of the hollow element.

In addition or alternatively, and in a ninth aspect, the radiopaque sleeve is configured to limit exposure of the medical implant to 4 gray or less of ionizing radiation when the medical implant is stored in the lumen of the hollow element and the containment vessel is exposed to 30 gray or more of ionizing radiation.

In addition or alternatively, and in a tenth aspect, the proximal end cap is threadably secured to the proximal end of the hollow element.

In addition or alternatively, and in an eleventh aspect, the medical implant is a replacement heart valve.

In addition or alternatively, and in a twelfth aspect, the secondary proximal end cap is threadably secured to the proximal end cap.

In addition or alternatively, and in a thirteenth aspect, the proximal end cap includes a sealing element disposed therein, the secondary proximal end cap being configured to compress the sealing element against an outer surface of the outer sheath.

In addition or alternatively, and in a fourteenth aspect, the proximal end cap includes a sheath receiving portion configured to matingly abut a distal end of the outer sheath.

In addition or alternatively, and in a fifteenth aspect, the sheathing guide includes a tapered surface extending from a distal end of the sheathing guide toward a proximal end of the proximal end cap.

In addition or alternatively, and in a sixteenth aspect, the tapered surface tapers radially inwardly from the distal end of the sheathing guide toward the proximal end of the proximal end cap.

In addition or alternatively, and in a seventeenth aspect, a minimum inner diameter of the sheathing guide is less than an inner diameter of the lumen of the outer sheath at the distal end of the lumen of the outer sheath.

In addition or alternatively, and in an eighteenth aspect, an accessory sheathing guide may include a first portion and a second portion configured to matingly engage with the first portion to define a tapered surface tapering radially inwardly from a distal end of the accessory sheathing guide toward a proximal end of the sheathing guide, and a first securing means and a second securing means configured to couple the first portion to the second portion.

In addition or alternatively, and in a nineteenth aspect, the first portion is pivotably connected to the second portion by a hinge element.

In addition or alternatively, and in a twentieth aspect, an accessory sheathing guide may include a first portion and a second portion configured to matingly engage with the first portion to define a tapered inner surface tapering from a maximum inner diameter adjacent a distal end of the accessory sheathing guide to a minimum inner diameter adjacent a proximal end of the sheathing guide, and a first securing means and a second securing means configured to releasably couple the first portion to the second portion. The first portion may be separable from and independent of the second portion.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments in connection with the accompanying drawings, in which:

FIGS. 11-12 illustrate an example accessory sheathing guide in use sheathing an example medical implant.

Figure 1:
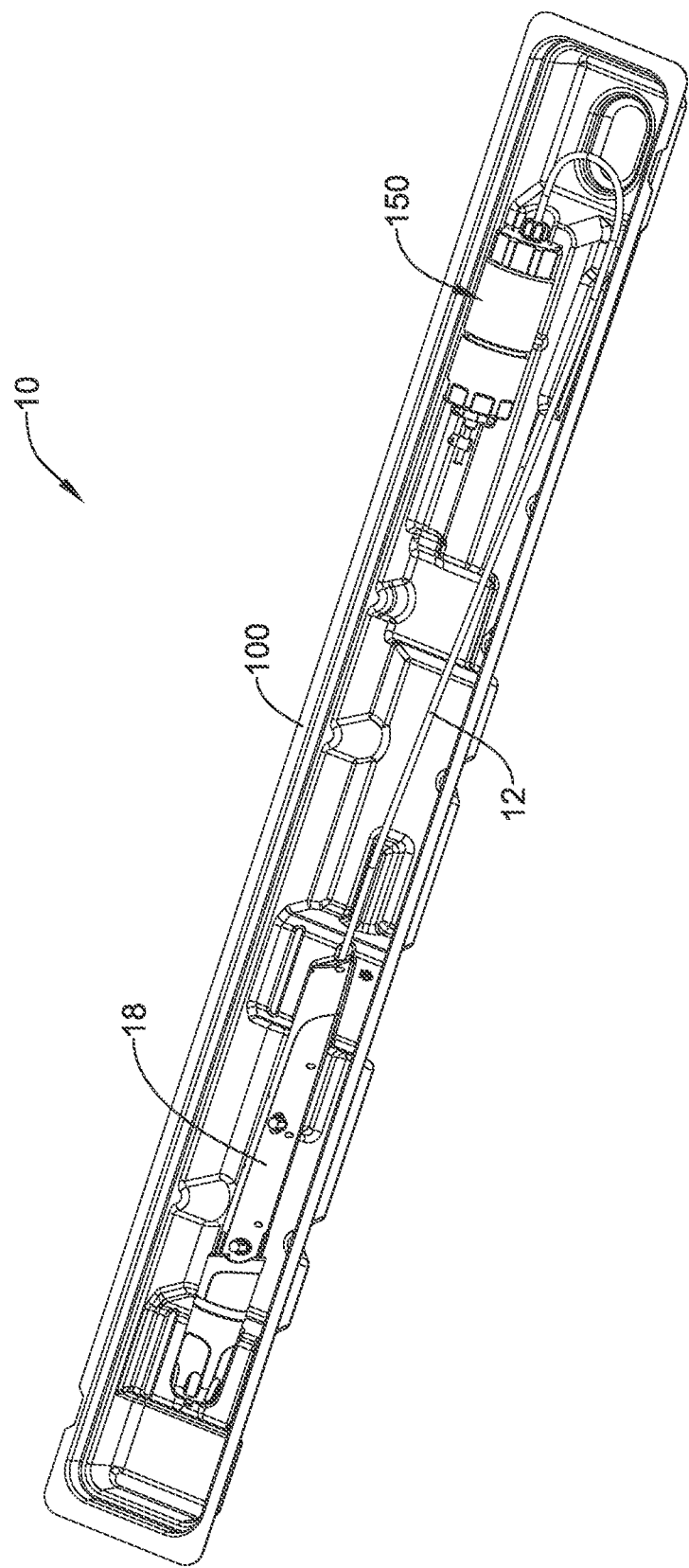
FIG. 1 illustrates an example medical device system and an example packaging apparatus.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. Other relative terms, such as "upstream", "downstream", "inflow", and "outflow" refer to a direction of fluid flow within a lumen, such as a body lumen, a blood vessel, or within a device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10, shown in FIG. 1, for example, within at least a portion of a packaging apparatus 100. In some embodiments, the packaging apparatus 100 may include a containment vessel 150 adapted to store and/or contain a medical implant, as discussed herein. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of the medical implant 16, such as a replacement heart valve (not visible in FIG. 1). This, however, is not intended to be limiting as the medical device system 10 may also be used for other interventions including valve repair, valvuloplasty, and the like, or other similar interventions.

Figure 2:
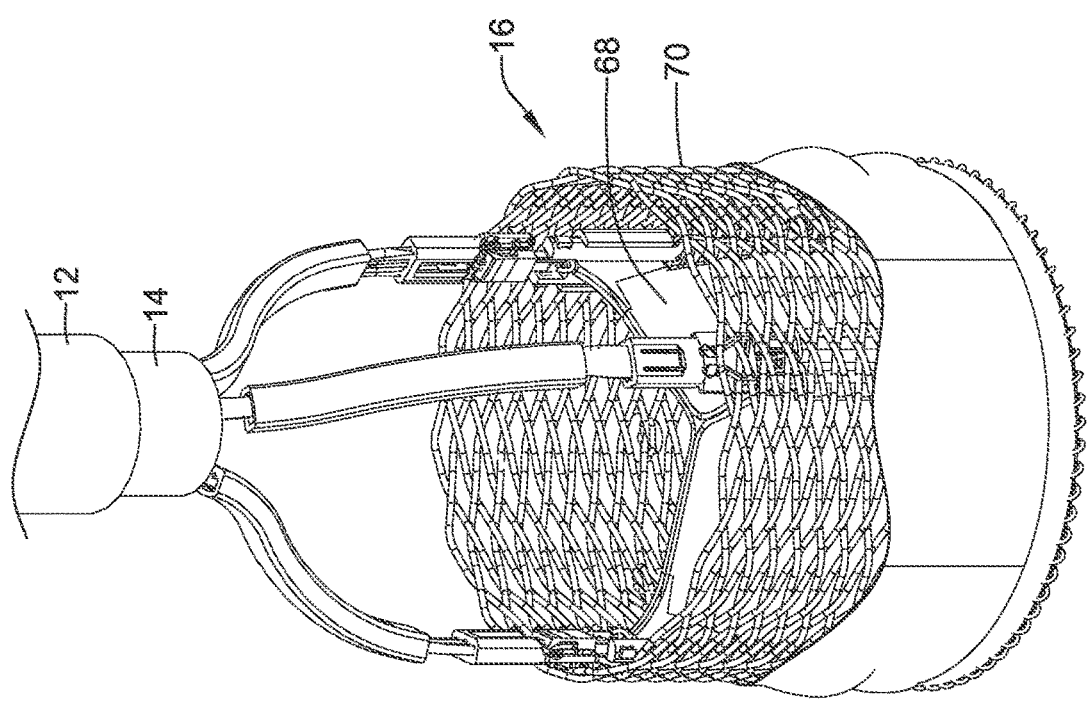
FIG. 2 illustrates an example medical implant associated with the medical device system.

The medical device system 10 may generally be described as a catheter system that includes an outer sheath 12, an inner catheter 14 extending at least partially through a lumen of the outer sheath 12, and a medical implant 16 (e.g., a replacement heart valve implant, for example, which term may be used interchangeably with the term "medical implant" herein) which may be coupled to the inner catheter 14, as seen in FIG. 2. In some embodiments, the medical implant 16 may include one or more biologically-derived and/or biologically compatible components. In some embodiments, the medical implant 16 may be configured to be disposed within a lumen of the outer sheath 12 during percutaneous delivery of the medical implant 16. In some embodiments, a medical device handle 18 may be disposed at a proximal end of the outer sheath 12 (as seen in FIG. 1) and/or the inner catheter 14 and may include one or more actuation means associated therewith. In general, the medical device handle 18 may be configured to manipulate the position of the outer sheath 12 relative to the inner catheter 14 and/or aid in the sheathing and/or the deployment of the medical implant 16. In some embodiments, the medical device system 10 may include a nose cone (not shown) extending distally from the inner catheter 14 and/or the outer sheath 12. In at least some embodiments, the nose cone may be designed to have an atraumatic shape.

In use, the medical device system 10 may be advanced percutaneously through the vasculature to a position adjacent to an area of interest and/or a treatment location (e.g., a position adjacent to a defective native valve such as an aortic valve, mitral valve, etc.). During delivery, the medical implant 16 may be generally disposed in an elongated and low profile "delivery" configuration within the lumen and/or a distal end of the outer sheath 12. Once positioned, the outer sheath 12 may be retracted relative to the medical implant 16 and/or the inner catheter 14 to expose the medical implant 16. The medical implant 16 may be actuated using the medical device handle 18 in order to translate the medical implant 16 into a generally shortened and larger profile "deployed" configuration suitable for implantation within the anatomy, as seen in FIG. 2 for example. When the medical implant 16 is suitably deployed within the anatomy, the medical device system 10 may be disconnected, detached, and/or released from the medical implant 16 and the medical device system 10 can be removed from the vasculature, leaving the medical implant 16 in place in a "released" configuration, to function as, for example, a suitable replacement for the native valve. In at least some interventions, the medical implant 16 may be deployed within the native valve (e.g., the native valve is left in place and not excised). Alternatively, the native valve may be removed and the medical implant 16 may be deployed in its place as a replacement.

FIG. 2 illustrates some selected components of the medical device system 10 and/or the medical implant 16 in the "deployed" configuration. For example, here it can be seen that the medical implant 16 includes one or more biologically-derived and/or biologically compatible components, for example, a plurality of valve leaflets 68 (e.g., bovine pericardial, porcine, polymeric, etc.) which may be secured to a tubular anchor member 70 that is reversibly actuatable between the "delivery" configuration and the "deployed" configuration. In some embodiments, the tubular anchor member 70 may define a central longitudinal axis extending from a proximal end of the tubular anchor member 70 to a distal end of the tubular anchor member 70, and/or a lumen extending through the tubular anchor member 70 along, parallel to, coaxial with, and/or coincident with the central longitudinal axis. In some embodiments, the tubular anchor member 70 may be and/or include a braid formed from one or more filaments or wires (e.g., a single filament or wire, two filaments, or wires, etc.). Other shapes and/or configurations are also contemplated. Some suitable but non-limiting materials for the tubular anchor member 70, for example metallic materials or polymeric materials, may be described below.

In some embodiments, at least one actuator member may be used to reversibly actuate (e.g., translate axially or longitudinally and/or expand radially) the medical implant 16 between the "delivery" configuration and the "deployed" configuration. In some embodiments, the medical device system 10 may include at least one actuator member extending from the medical device handle 18 to the medical implant 16. In some embodiments, the at least one actuator member may include a plurality of actuator members (for example, three actuator members, or another suitable or desired number of actuator members). In some embodiments, the at least one actuator member may be configured to engage with a plurality of locking mechanisms and actuate the tubular anchor member 70 and/or the medical implant 16 between the "delivery" configuration, the "deployed" configuration, and/or a "released" configuration.

In some embodiments, a seal member may be circumferentially disposed on and/or about a distal portion and/or an inflow portion of the tubular anchor member 70, and as the term suggests, may help to seal an exterior of the medical implant 16 and/or the tubular anchor member 70 within and/or against a target site or area of interest upon deployment (e.g., in the "deployed" configuration and/or the "released" configuration), thereby preventing leakage around the medical implant 16 and/or the tubular anchor member 70. In some embodiments, the seal member may be disposed about, on, and/or radially outward of an outside surface of the tubular anchor member 70.

In some embodiments, attachment between the medical implant 16 and the inner catheter 14 (and/or the outer sheath 12) may be effected through the use of a coupler. The coupler may generally include a cylindrical base (not shown) that may be disposed about, attached to, and/or extending from a distal end of the inner catheter 14 (and/or the outer sheath 12). Projecting distally from the base is a plurality of fingers (e.g., two fingers, three fingers, four fingers, etc.) that are each configured to engage with the medical implant 16 at one of the plurality of locking mechanisms. Other suitable configurations are also contemplated. Some suitable but non-limiting materials for the coupler, the fingers, for example metallic materials or polymeric materials, may be described below.

During storage and/or transportation, the medical device system 10 may be disposed within the packaging apparatus 100. Within the packaging apparatus 100, the medical implant 16 of the medical device system 10 may be disposed within the containment vessel 150 in "partially-deployed" configuration. In some embodiments, the containment vessel 150 may be configured and adapted to contain at least one biocidal fluid therein. In some embodiments, the biocidal fluid may be disposed and/or contained within the outer sheath 12 and/or the inner catheter 14, which may be in fluid communication with the containment vessel 150. In some embodiments, the biocidal fluid may contain and/or include, for example, glutaraldehyde which may serve to sterilize the contacted surfaces of the system and which optionally may cross-link the biologically-derived and/or biologically compatible components of the medical implant 16.

In some embodiments, the containment vessel 150 may be a dual sterilization containment vessel configured and adapted to contain at least one sterilizing biocidal fluid as well as to allow ionizing radiation sterilization of the contents of the containment vessel 150 and/or other components of the medical device system 10 without undue damage to the biologically-derived and/or biologically compatible components of the medical implant 16. In some embodiments, materials selected to construct the containment vessel 150 may be substantially unreactive with the at least one biocidal fluid.

Figure 3:
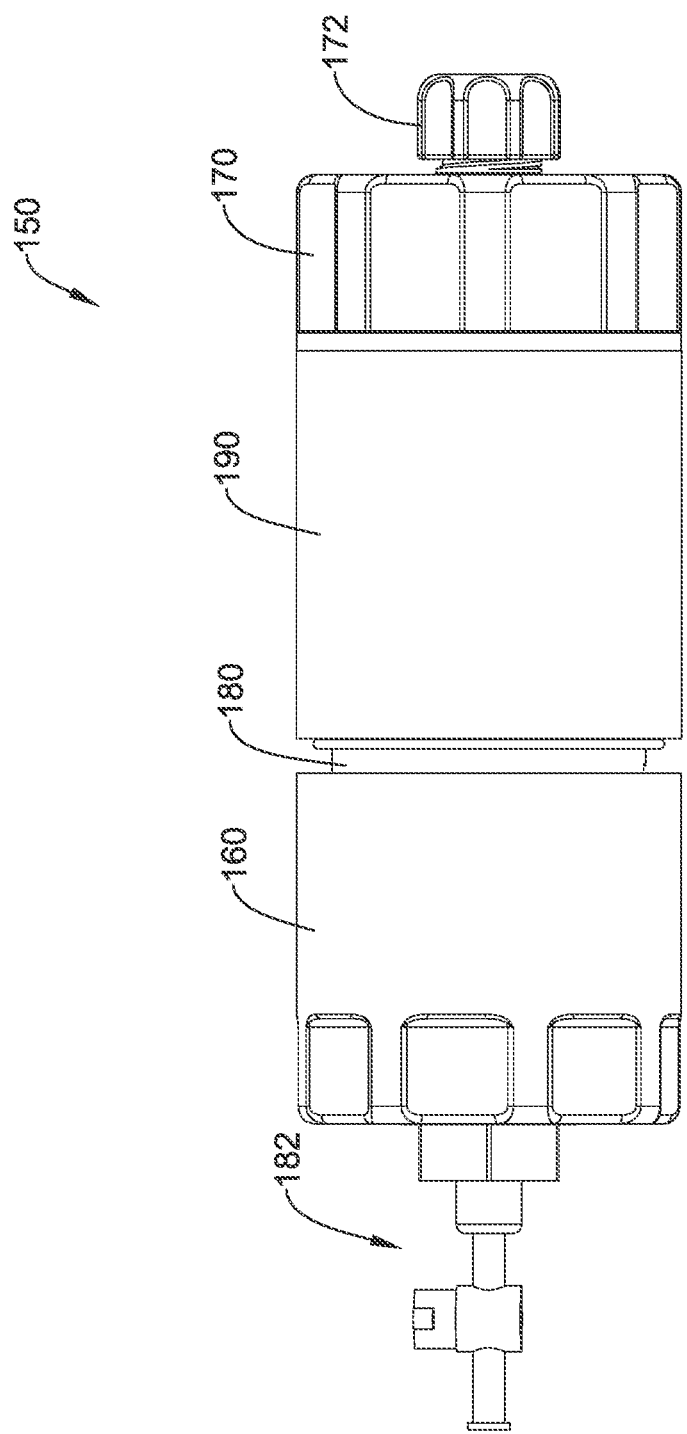
FIG. 3 illustrates an example containment vessel.

As shown in FIG. 3, the containment vessel 150 may include a radiopaque sleeve 190, for example. In some embodiments, the radiopaque sleeve 190 may prevent ionizing radiation applied to the medical device system 10 from reaching and/or damaging the biologically-derived and/or biologically compatible components of the medical implant 16. In some embodiments, the radiopaque sleeve 190 may be removable from, or alternatively may be permanently attached to, one or more other components of the containment vessel 150.

In some embodiments, the radiopaque sleeve 190 may be disposed within the containment vessel 150 to ensure that a space between the radiopaque sleeve 190 and the sterilization containment vessel 150 remains sterile. In some embodiments, one or more joints between the radiopaque sleeve 190 disposed externally of and/or around the containment vessel 150 may be sealed, for example by an O-ring, gasket, sealant, or the like to isolate a space between the radiopaque sleeve 190 and the containment vessel 150 and maintain a sterile environment therein. In some embodiments, the radiopaque sleeve 190 may be integrally formed with and/or within the containment vessel 150 to eliminate any exposed interface which might harbor contamination.

In some embodiments, the use of a dual sterilization containment vessel may be desirable when some components of the medical device system 10 other than the medical implant 16 require exposure to high levels of ionizing radiation to ensure that biocidal dosage levels are delivered to all internal parts of the system. Additionally, in some embodiments, the use of two separate sterilization methods, enabled by the presence of a dual sterilization containment vessel with the system may substantially reduce risk of bioactive contamination.

Figure 4:
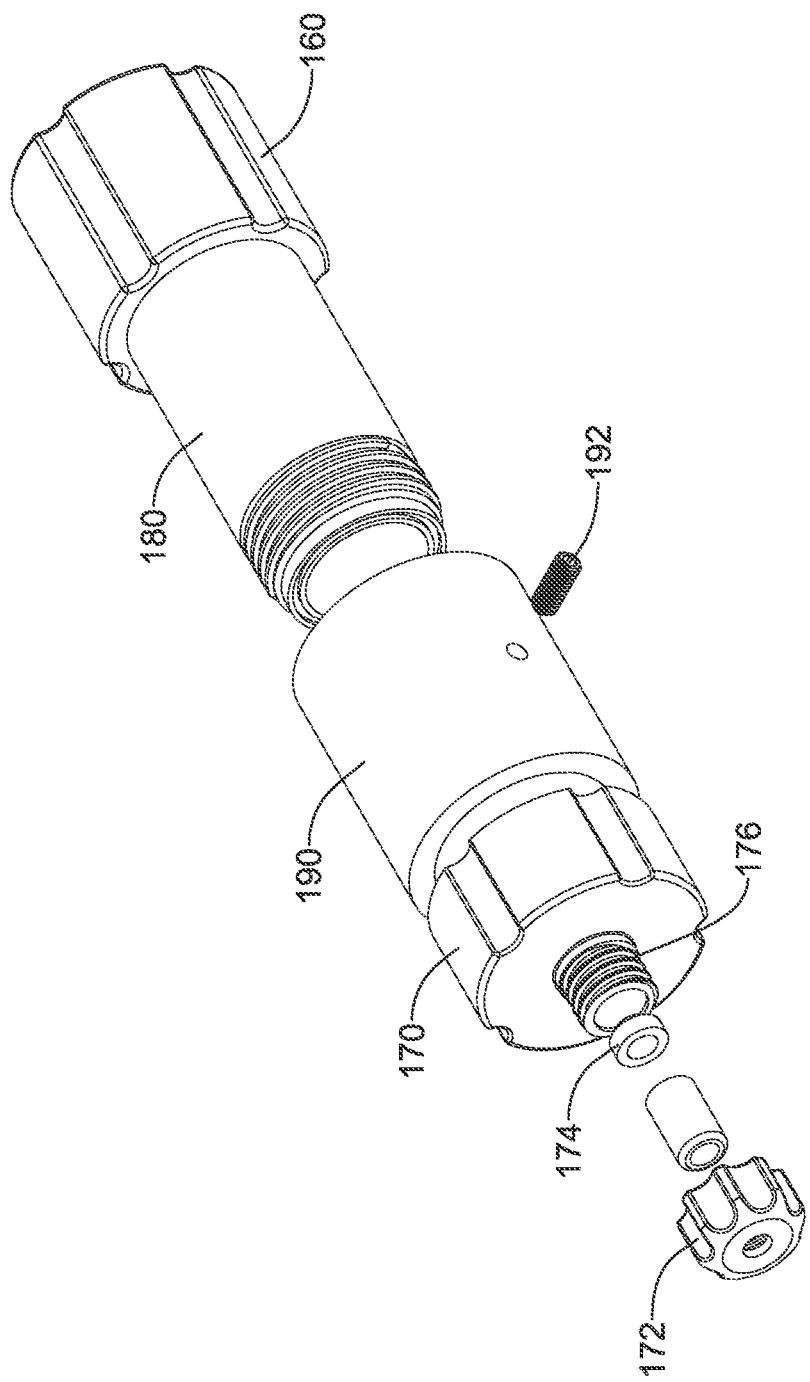
FIG. 4 is an exploded view of the example containment vessel of FIG. 3.

FIGS. 3 and 4 illustrate selected components of the example containment vessel 150 in assembled and exploded views, respectively. In some embodiments, the containment vessel 150 may include a hollow element 180 having a wall, a proximal end, a distal end, and a lumen extending between the proximal end and the distal end, wherein the lumen may be configured and adapted to contain a medical implant 16 and/or at least a portion of a delivery system configured and adapted to position and implant the medical implant 16 within a target site (e.g., a native heart valve, etc.). In some embodiments, the containment vessel 150 may include a distal end cap 160 removably and threadably engaged with the hollow element 180 and a proximal end cap 170 removably and threadably engaged with the hollow element 180. Other engagement means are also contemplated.

In some embodiments, the proximal end cap 170 may include a secondary proximal end cap 172 and a sealing element 174 configured and adapted to reversibly seal the proximal end cap 170 to the outer sheath 12 of the medical device system 10. In some embodiments, the secondary proximal end cap 172 may be rotatably engaged with a threaded neck 176 extending proximally from the proximal end cap 170. In some embodiments, a combination of the hollow element 180, the distal end cap 160, the proximal end cap 170, the secondary proximal end cap 172, the sealing element 174, the outer sheath 12, and the medical device handle 18 may form a fluid tight system providing a continuous fluid connection between an interior and/or the lumen of the hollow element 180 and the lumen of the outer sheath 12. In some embodiments, the hollow element 180 and/or the distal end cap 160 may include an outlet or a stopcock 182 configured to permit filling and/or draining of the one or more biocides from the medical device system 10 prior to removal of the medical implant 16 from the containment vessel 150 and/or the lumen of the hollow element 180.

In some embodiments, the containment vessel 150 and/or the hollow element 180 may be sized and/or have sufficient internal volume to contain the medical implant 16 in a partially-deployed configuration, wherein in the partially-deployed configuration the medical implant 16 and/or components of the medical implant 16 are fully and/or sufficiently exposed to the one or more biocidal fluids disposed within the containment vessel 150 and/or the lumen of the hollow element 180. Although illustrated as being generally cylindrical in configuration and/or construction, the hollow element 180 may be formed with a different shape and/or configuration as necessary or desired. In some embodiments, the hollow element 180 may have a unitary structure, while in other embodiments, the hollow element 180 may be formed as multiple element or pieces that are suitably sealed when joined together. For example, in some embodiments, the hollow element 180 may be formed as a clam-shell structure including two half-cylindrical wall pieces joined along a separable longitudinal seam with a suitable gasket or other sealing element disposed between the two half-cylindrical wall pieces.

As discussed herein, materials for use in constructing the containment vessel 150, the hollow element 180, the distal end cap 160, and/or the proximal end cap 170, etc. may be substantially unreactive with the one or more biocidal fluids. In some embodiments, the material(s) may be partially or fully transparent to visible light to permit visual inspection of the medical implant 16 and/or other contents of the containment vessel 150 and/or the hollow element 180. In some embodiments, the material(s) may remain substantially unchanged chemically and/or mechanically upon exposure to and/or absorption of ionizing radiation at levels of 30 to 50 gray or more, for example, when the containment vessel 150 and/or the hollow element 180 is empty and/or when the containment vessel 150 and/or the lumen of the hollow element 180 is filled with the one or more biocidal fluids. In some embodiments, at least a portion of an interior surface of at least one of the hollow element 180, the distal end cap 160, and/or the proximal end cap 170 may include a polished surface in fluid communication with the lumen of the hollow element 180. In some embodiments, the polished surface may facilitate removal of bubbles from the one or more biocidal fluids disposed within the containment vessel 150. In some embodiments, the hollow element 180 may include one or more features configured and adapted to direct the motion of bubbles which may be present within the containment vessel 150 when it is filled with the one or more biocidal fluids and/or when it is subjected to changes in orientation. In some embodiments, the one or more features configured and adapted to direct the motion of bubbles may include ridges, grooves, tapers, and/or combinations thereof, for example. Other configurations are also contemplated.

As mentioned above, the distal end cap 160 and/or the proximal end cap 170 may be reversibly secured to the hollow element 180 by mating threaded sections. In some embodiments, the hollow element 180 may include external and/or male threads disposed adjacent the proximal end and/or the distal end, and the distal end cap 160 and/or the proximal end cap 170 may include corresponding female threads therein. Other configurations, including but not limited to reversal of the thread orientations, are also contemplated.

In some embodiments, the radiopaque sleeve 190 may include a lumen extending therethrough that substantially matches and/or corresponds to the exterior shape and/or dimension of the hollow element 180. In some embodiments, the radiopaque sleeve 90 may include a radiopaque solid material and/or a radiopaque fluid or gel. In some embodiments, the radiopaque sleeve 190 may be secured to the hollow element 180 by, for example, a set screw 192 during at least a portion of the sterilization process. Alternatively, in some embodiments, the radiopaque sleeve 190 may be formed from several pieces and held in place by a clamping element or other suitable means (not shown). In such embodiments, the pieces may include overlapping regions along the joints or seams to ensure that higher than desirable amounts of ionizing radiation do not reach the medical implant 16. In some embodiments, the radiopaque sleeve 190 may be permanently attached to one or more of the other components of the containment vessel 150. The radiopacity of the radiopaque sleeve 190 may be selected such that in combination with the hollow element 180, the medical implant 16 may absorb no more than 4 gray of ionizing radiation when the containment vessel 150 is exposed to 30 to 50 gray or more of ionizing radiation, whether the containment vessel 150 is empty or filled with the one or more biocidal fluids.

In some embodiments, the distal end cap 160 and/or the proximal end cap 170 may be sized and configured to retain the radiopaque sleeve 190 in position about the hollow element 180. However, in some embodiments, the radiopaque sleeve 190 may be configured to be removed from the hollow element 180 without removing one or both of the distal end cap 160 and/or the proximal end cap 170. In such embodiments, a set screw or other retaining element may be utilized to retain the radiopaque sleeve 190 in position about the hollow element 180.

Figure 5:
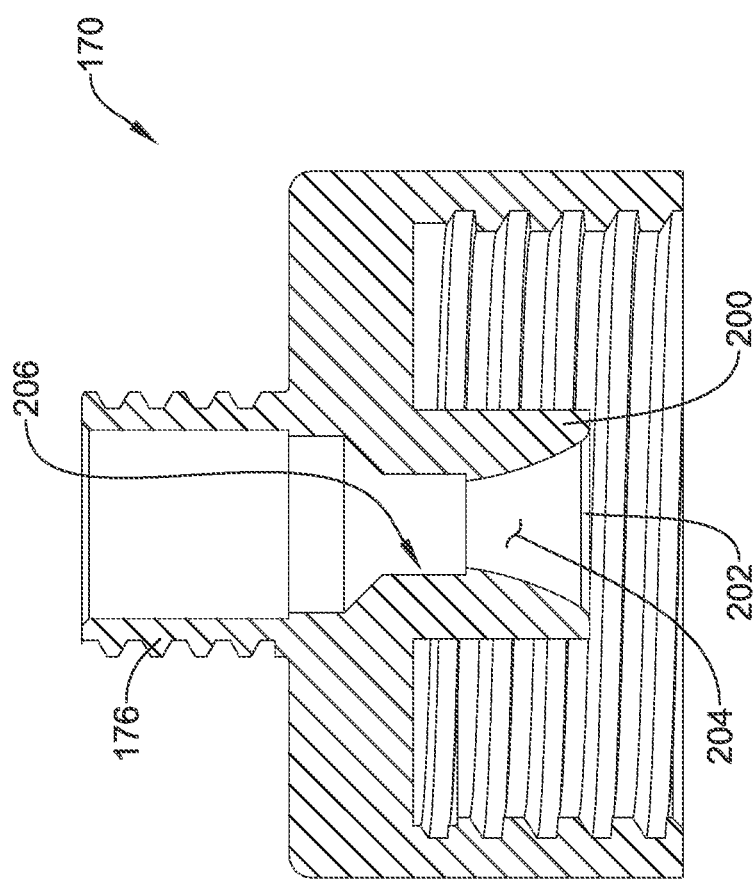
FIG. 5 is a cross-sectional view of an example proximal end cap.

FIG. 5 illustrates a cross-sectional view of the example proximal end cap 170. As seen in FIG. 5, the proximal end cap 170 may include a sheathing guide 200 integrally formed therewith. In some embodiments, when the proximal end cap 170 is threadably and/or matingly engaged with the hollow element 180, the sheathing guide 200 may extending into the lumen of the hollow element 180 and/or an interior of the containment vessel 150.

In some embodiments, the sheathing guide 200 may include a tapered surface 204 (e.g., linearly tapered, gradually tapered, arcuately tapered, trumpet-like, etc.) extending proximally from a distal end 202 of the sheathing guide 200 toward a sheath receiving portion 206 of the proximal end cap 170. In some embodiments, the sheath receiving portion 206 of the proximal end cap 170 may be sized and configured to accept and/or matingly engage a distal end of the outer sheath 12. In some embodiments, the sheath receiving portion 206 of the proximal end cap 170 may include a proximally-facing surface and/or wall configured to abut the distal end of the outer sheath 12 when the outer sheath 12 extends through the threaded neck 176 and is received within the sheath receiving portion 206 of the proximal end cap 170. In some embodiments, the proximally-facing surface and/or wall may include an opening therethrough configured to fluidly connect the lumen of the outer sheath 12 with the tapered surface 204, the lumen of the hollow element 180, and/or the interior of the containment vessel 150.

In some embodiments, the tapered surface 204 may have a variable radius. In some embodiments, the distal end 202 of the sheathing guide 200 may define a maximum inner diameter of the tapered surface 204. In some embodiments, the opening and/or a proximal end of the sheathing guide 200 may define a minimum inner diameter of the tapered surface 204. In some embodiments, the minimum inner diameter of the tapered surface 204 may be less than an inner diameter of the lumen of the outer sheath 12 at the distal end of the outer sheath 12 and/or the lumen of the outer sheath 12.

Figure 9:
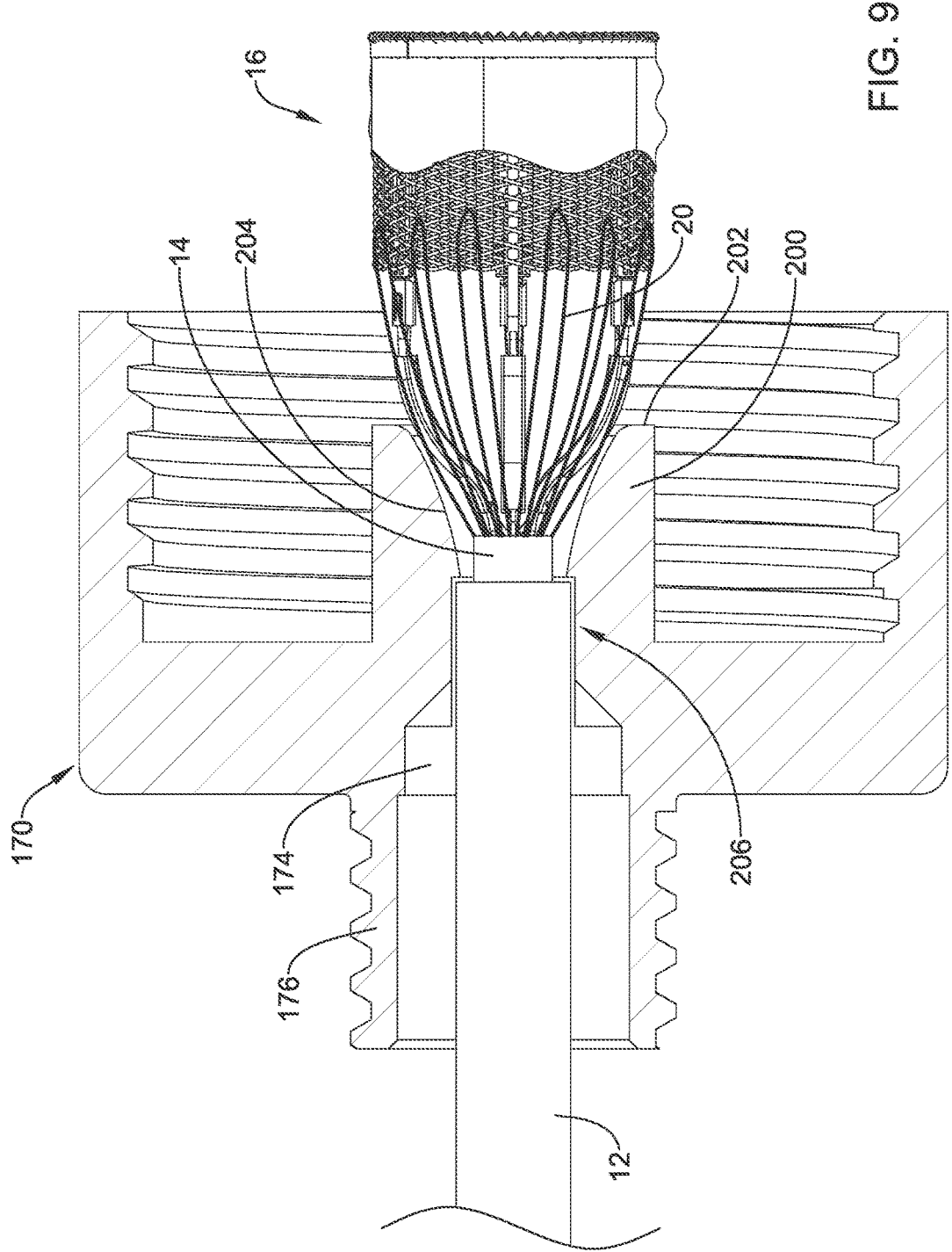
FIGS. 9-10 illustrate an example proximal end cap in use sheathing an example medical implant.
Figure 10:
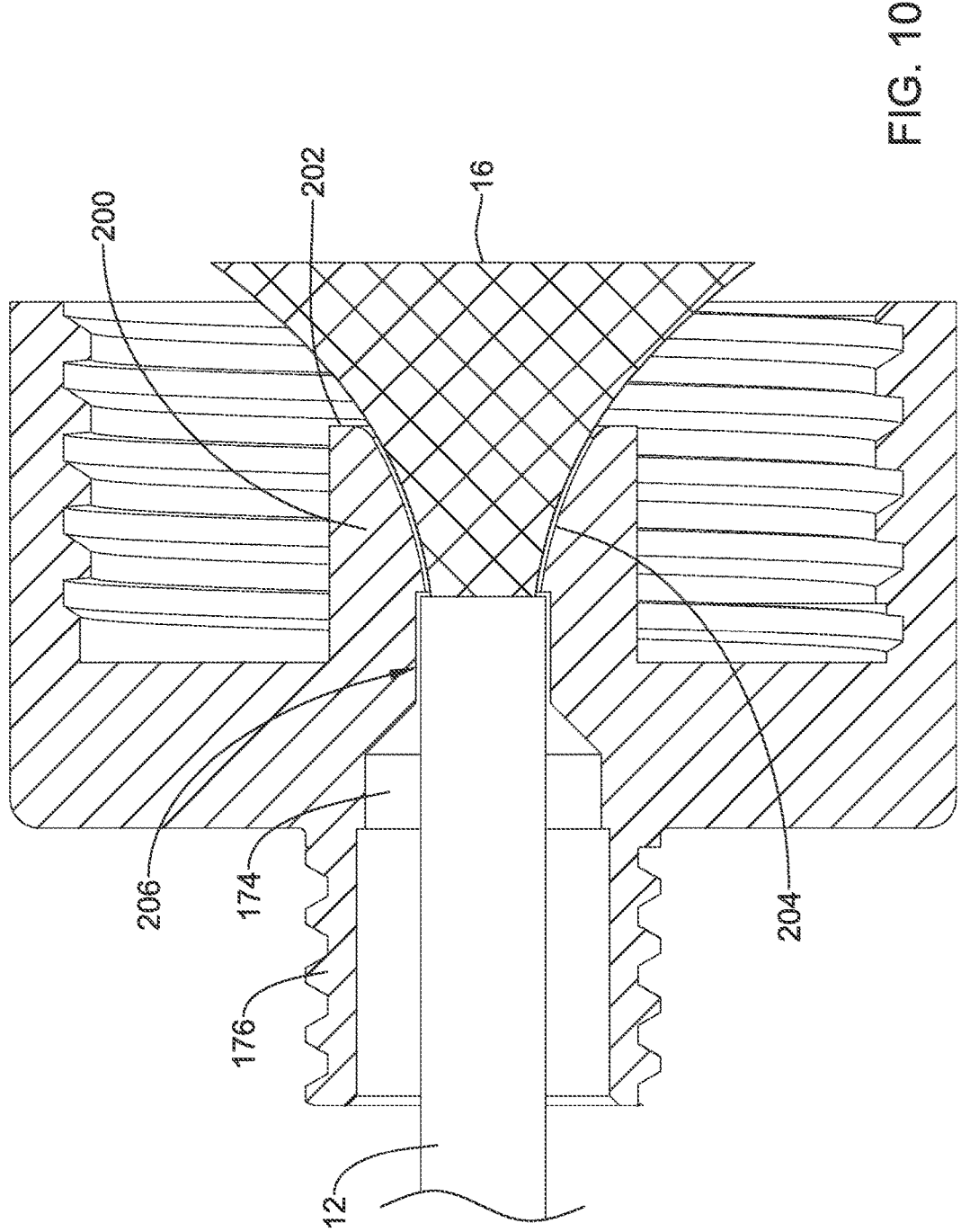

In at least some embodiments, the tapered surface 204 of the sheathing guide 200 may guide and radially compress a medical implant 16 passing (e.g., being withdrawn, translated proximally, etc.) therethrough in a proximal direction into the lumen of the outer sheath 12 during sheathing of the medical implant 16, as seen in FIGS. 9 and 10 for example. In FIG. 9, the example medical implant 16 is shown as it may be disposed within the containment vessel 150 distal of the proximal end cap 170 in a partially-deployed configuration. In some embodiments, the medical device system 10 may optionally include a sheathing aid 20 extending distally from the inner catheter 14 and configured to guide a proximal end of the medical implant 16 into the outer sheath 12. As would be apparent to the skilled practitioner, the sheathing aid 20 need not be present in all embodiments. FIG. 10 illustrates an example medical implant 16 partially sheathed and/or partially translated within the lumen of the outer sheath 12 of an example medical device system 10. As can be seen schematically in FIG. 10, as the medical implant 16 is withdrawn into the distal end of the outer sheath 12, the medical implant 16 is actuated and/or compressed toward an elongated delivery configuration, wherein in the delivery configuration, the medical implant 16 is radially compressed and assumes a smaller outer diameter and/or a longer overall length compared to the deployed configuration shown in FIG. 2 and/or the partially deployed configuration shown in FIG. 9. When the medical implant 16 is fully disposed within the lumen of the outer sheath 12, the medical implant 16 may be considered to be in the delivery configuration.

In some embodiments, a proximal end cap 170 including the sheathing guide 200 may permit the medical implant 16 to be sheathed within the lumen of the outer sheath 12 directly from and/or while the outer sheath 12 is coupled to the containment vessel 150, thereby preventing exposure of the medical implant 16 to the outside environment, airborne contaminants, etc.

Figure 6:
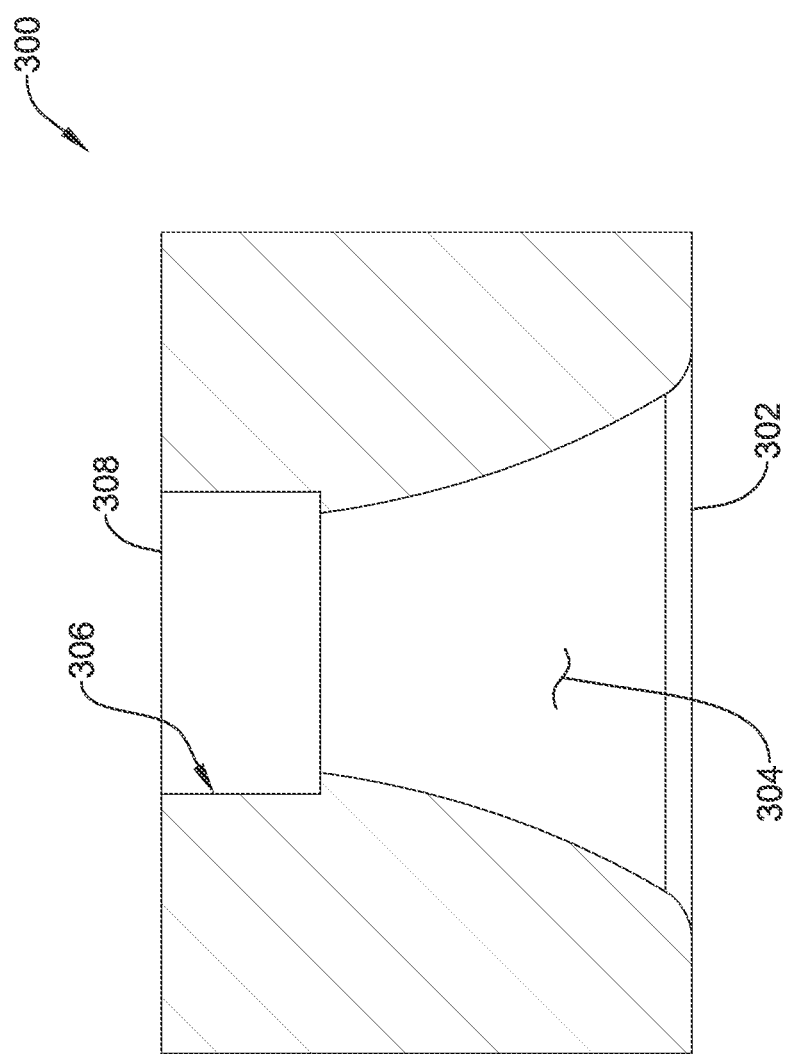
FIG. 6 is a cross-sectional view of an example accessory sheathing guide.

Turning to FIG. 6, a cross-sectional view of an accessory sheathing guide 300 is illustrated. In some embodiments, an accessory sheathing guide 300 may be provided within the packaging apparatus 100 along with the medical device system 10. In some embodiments, an accessory sheathing guide 300 may be provided separately from the packaging apparatus 100 and/or the medical device system 10, and may be suitable for use with a variety of different compatible medical devices and/or systems.

In some embodiments, an accessory sheathing guide 300 may be configured and adapted to matingly engage with and/or secure to a distal end of the outer sheath 12 of the medical device system 10. The accessory sheathing guide 300 may include a proximal end 308 and a distal end 302. In some embodiments, the accessory sheathing guide 300 may include a tapered surface 304 (e.g., linearly tapered, gradually tapered, arcuately tapered, trumpet-like, etc.) extending proximally from the distal end 302 of the accessory sheathing guide 300 toward a sheath receiving portion 306 of the accessory sheathing guide 300. In some embodiments, the sheath receiving portion 306 of the accessory sheathing guide 300 may be sized and configured to accept and/or matingly engage a distal end of the outer sheath 12. In some embodiments, the sheath receiving portion 306 of the accessory sheathing guide 300 may include a proximally-facing surface and/or wall configured to abut the distal end of the outer sheath 12 when the outer sheath 12 extends through the proximal end 308 of accessory sheathing guide 300 and is received within the sheath receiving portion 306 of the accessory sheathing guide 300. In some embodiments, the proximally-facing surface and/or wall may include an opening therethrough configured to fluidly connect the lumen of the outer sheath 12 and/or the sheath receiving portion 306 with the tapered surface 304.

In some embodiments, the tapered surface 304 may have a variable radius. In some embodiments, the distal end 302 of the accessory sheathing guide 300 may define a maximum inner diameter of the tapered surface 304. In some embodiments, the opening in the proximally-facing surface and/or wall at the sheath receiving portion 306 may define a minimum inner diameter of the tapered surface 304. In some embodiments, the minimum inner diameter of the tapered surface 304 may be less than an inner diameter of the lumen of the outer sheath 12 at the distal end of the outer sheath 12 and/or the lumen of the outer sheath 12.

Figure 11:
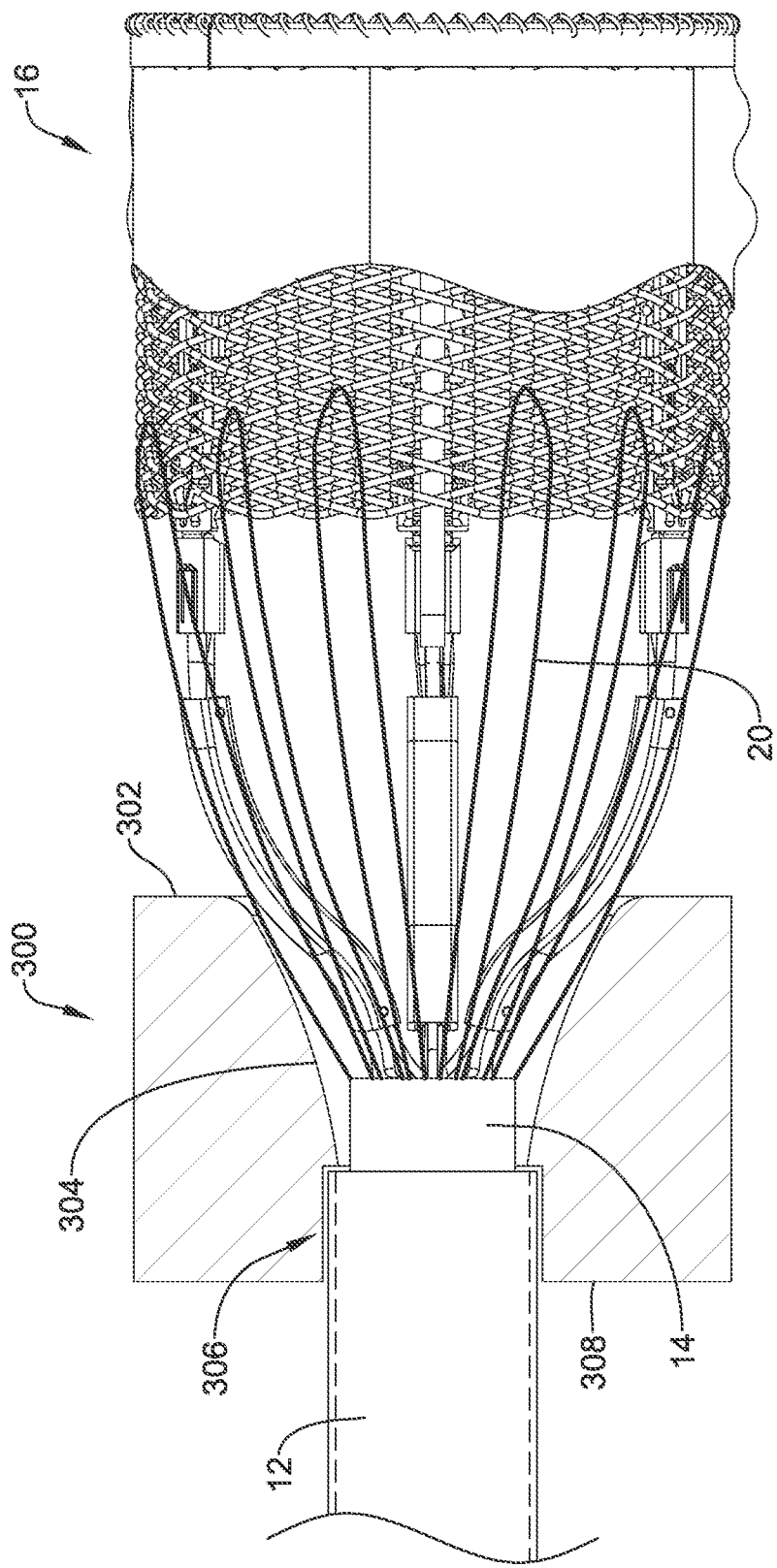

In at least some embodiments, the tapered surface 304 of the accessory sheathing guide 300 may guide and radially compress a medical implant 16 passing (e.g., being withdrawn, translated proximally, etc.) therethrough in a proximal direction into the lumen of the outer sheath 12 during sheathing of the medical implant 16, as seen in FIGS. 11 and 12 for example. In FIG. 11, the example medical implant 16 is shown in a partially-deployed configuration distal of the outer sheath 12 and/or the accessory sheathing guide 300. In some embodiments, the medical device system 10 may optionally include a sheathing aid 20 extending distally from the inner catheter 14 and configured to guide a proximal end of the medical implant 16 into the outer sheath 12. As would be apparent to the skilled practitioner, the sheathing aid 20 need not be present in all embodiments. FIG. 12 illustrates an example medical implant 16 partially sheathed and/or partially translated within the lumen of the outer sheath 12 of an example medical device system 10. As can be seen schematically in FIG. 12, as the medical implant 16 is withdrawn into the distal end of the outer sheath 12, the medical implant 16 is actuated and/or compressed toward an elongated delivery configuration, wherein in the delivery configuration, the medical implant 16 is radially compressed and assumes a smaller outer diameter and/or a longer overall length compared to the deployed configuration shown in FIG. 2 and/or the partially deployed configuration shown in FIG. 11. When the medical implant 16 is fully disposed within the lumen of the outer sheath 12, the medical implant 16 may be considered to be in the delivery configuration.

Figure 7:
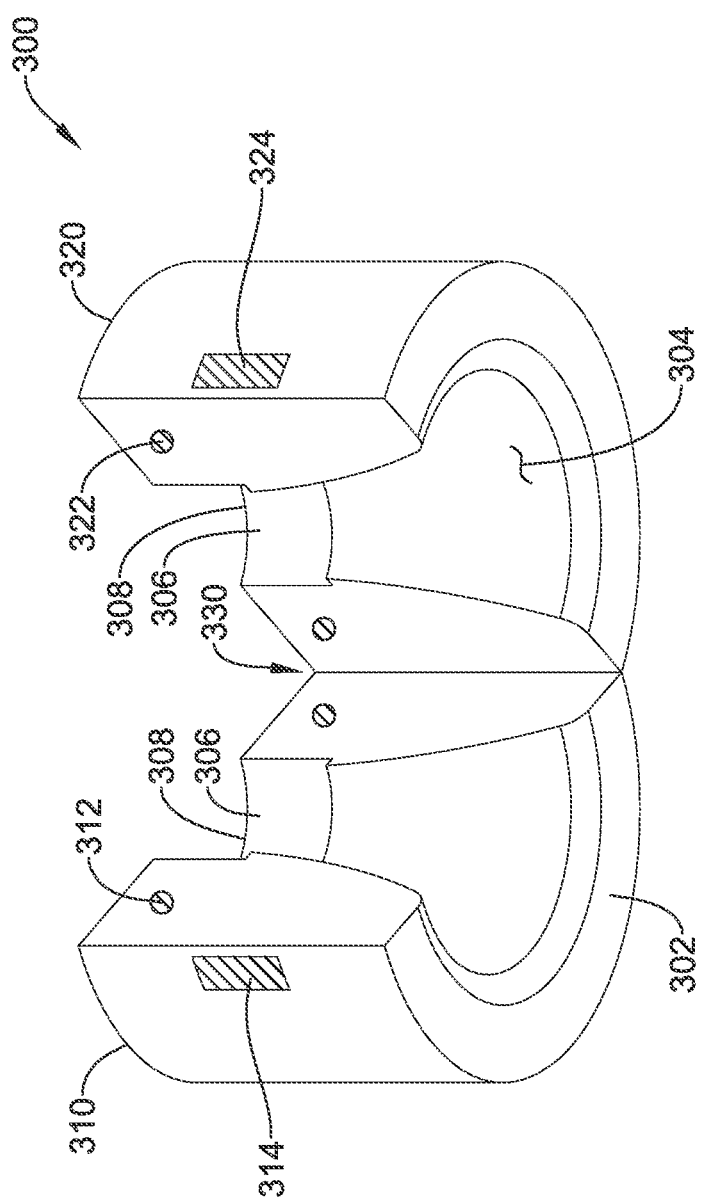
FIGS. 7-8 illustrate example configurations of the example accessory sheathing guide of FIG. 6.
Figure 8:
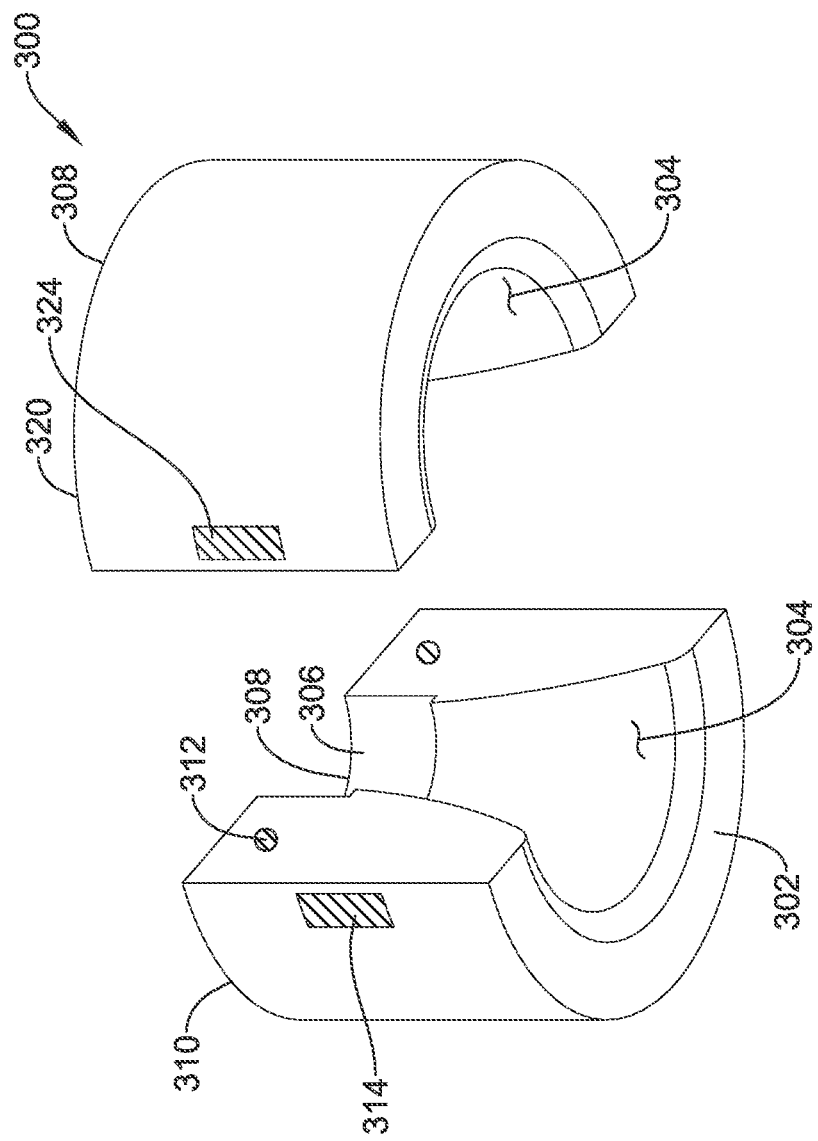

As shown in FIG. 7, the accessory sheathing guide 300 may include a first portion 310 and a second portion 320 configured to be coupled together in mating abutment to define the tapered surface 304. In some embodiments, the first portion 310 and the second portion 320 may be configured to "open" or spread apart to facilitate coupling the accessory sheathing guide 300 to the distal end of the outer sheath 12. In some embodiments, the first portion 310 and the second portion 320 may be configured in a clam shell arrangement. In some embodiments, the first portion 310 and the second portion 320 may be pivotably joined together at and/or by a hinge element 330. In some embodiments, as seen in FIG. 8 for example, the first portion 310 and the second portion 320 may be separable pieces and/or independent from each other.

In some embodiments, the first portion 310 may include a first plurality of fastener elements 312 and the second portion 320 may include a second plurality of fastener elements 322, the first plurality of fastener elements 312 and the second plurality of fastener elements 322 being configured to accept a mechanical fastener (e.g., a screw, bolt, etc.) therein to couple the first portion 310 to the second portion 320. In some embodiments, the first plurality of fastener elements 312 and/or the second plurality of fastener elements 322 may include apertures or holes, threaded apertures or holes, slots, and/or other features. In some embodiments, the first plurality of fastener elements 312 may extend partially or completely through the first portion 310, and/or the second plurality of fastener elements 322 may extend partially or completely through the second portion 320. In some embodiments, the first plurality of fastener elements 312 may align with the second plurality of fastener elements 322.

In addition or alternatively, in some embodiments, the first portion 310 may include a first securing means 314 and the second portion 320 may include a second securing means 324, the first securing means 314 and the second securing means 324 being configured to couple the first portion 310 to the second portion 320. In some embodiments, the first portion 310 may include more than one first securing means 314 and/or the second portion 320 may include more than one first securing means 324. In some embodiments, the first securing means 314 and the second securing means 324 may each comprise a magnet and/or a magnetic element. In some embodiments, the first securing means 314 and the second securing means 324 may each comprise a portion of a clamp or other mechanical latching means. In some embodiments, the first securing means 314 may be at least partially embedded within the first portion 310 and/or the second securing means 324 may be at least partially embedded within the second portion 320. In some embodiments, the first securing means 314 may be fixedly or removably attached to an outer surface of the first portion 310. In some embodiments, the second securing means 324 may be fixedly or removably attached to an outer surface of the second portion 320. In some embodiments, the first securing means 314 and the second securing means 324 may, individually or in combination, surround the first portion 310 and the second portion 320 when the first portion 310 is in mating abutment with the second portion 320.

One possible non-limiting use sequence for a containment vessel 150 may be described as follows. The medical implant 16 and associated components configured and adapted to position and install the medical implant 16 may be withdrawn within the outer sheath 12, whereupon a proximal end cap 170 of a containment vessel 150 may be positioned to partially encompass the distal end of the outer sheath 12. Once the proximal end cap 170 is secured to the distal end of the outer sheath 12 by the secondary proximal end cap 172 and the sealing element 174, the medical implant 16 and associated components configured and adapted to position and install the medical implant 16 may be advanced from the distal end of the outer sheath 12 until it achieves an expanded and/or a partially deployed configuration, such as that of FIG. 2. Continuous and/or fluidly connected lumen(s) joining the medical device handle 18, the outer sheath 12, and the containment vessel 150 (e.g., the hollow element 180, etc.) may then be filled with one or more biocidal fluids, such as an alcoholic gluteraldehyde solution, and flushed to remove bubbles and any incidentally introduced debris. Following flushing, the outlet or the stopcock 182 and/or a corresponding outlet or stopcock associated with the medical device handle 18 may be closed to seal and contain the one or more biocidal fluids within the medical device system 10 and the containment vessel 150.

The closed system may be placed in the packaging apparatus 100 and exposed to a source of ionizing radiation of sufficient penetrating power and for a sufficient time to sterilize the contents of the packaging apparatus 100. The radiopaque sleeve 190 may serve to limit the ionizing radiation absorbed by the biologically-derived and/or biologically compatible component(s) and/or the medical implant 16. In some embodiments, the ionizing radiation absorbed by the biologically-derived and/or biologically compatible component(s) and/or the medical implant 16 may be less than 4 gray when the medical device system 10 as a whole has been exposed to 30 to 50 gray or more of ionizing radiation. At this point, it will be appreciated that the contents of the medical device system 10 have been sterilized by two independent methods and is ready for storage and distribution prior to use in a heart valve replacement procedure, for example. The containment vessel 150 may be configured and adapted to maintain and/or store the biologically-derived and/or biologically compatible component(s) and/or the medical implant 16 within the lumen of the hollow element 180 in a hydrating and sterile environment (e.g., in a wet condition) prior to use.

When the stored medical implant 16 and/or the medical device system 10 is to be used, the medical implant 16 may be rinsed within the containment vessel 150 with a sterile and/or biologically-compatible rinsing fluid, such as saline for example, by connecting a source of rinsing fluid to the medical device handle 18 in fluid communication with the lumen of the outer sheath 12 and the lumen of the hollow element 180 of the containment vessel 150. The outlet or stopcock 182 may be opened to release storage fluid (e.g., the one or more biocidal fluids) from within the containment vessel 150. Rinsing fluid may then be injected and/or fed under pressure into the containment vessel 150 from the source of rinsing fluid, thereby rinsing the one or more biocidal fluids from the medical implant 16 and/or internal components of the medical device system 10. The outlet or stopcock 182 may be left open to permit the rinsing fluid to pass through the containment vessel 150 and/or be released from within the lumen of the hollow element 180.

After rinsing the medical implant 16, the medical implant 16 may be sheathed within and/or translated proximally into the lumen of the outer sheath 12 from the partially-deployed configuration to the delivery configuration for percutaneous insertion to a target site.

The materials that can be used for the various components of the medical device system 10, the containment vessel 150, etc. (and/or other systems disclosed herein) and the various elements thereof disclosed herein may include those commonly associated with medical devices. For simplicity purposes, the following discussion makes reference to the delivery system and/or the medical implant 16. However, this is not intended to limit the devices and methods described herein, as the discussion may be applied to other elements, members, components, or devices disclosed herein, such as, but not limited to, the tubular anchor member 70, the actuator members, and/or elements or components thereof.

In some embodiments, the delivery system and/or the medical implant 16, and/or components thereof (such as, but not limited to, the tubular anchor member 70, the actuator members, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery system and/or the medical implant 16, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the delivery system and/or the medical implant 16. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery system and/or the medical implant 16 to achieve the same result.

In some embodiments, a degree of Magnetic Resonance Imaging (MRI) compatibility is imparted into the medical implant 16. For example, the delivery system and/or the medical implant 16, and/or components or portions thereof, may be made of a material that does not substantially distort the image and create substantial artifacts (e.g., gaps in the image). Certain ferromagnetic materials, for example, may not be suitable because they may create artifacts in an MRI image. The delivery system and/or the medical implant 16, or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, a sheath or covering (not shown) may be disposed over portions or all of the delivery system and/or the medical implant 16. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A containment vessel for storing and sterilizing a medical implant coupled to a delivery system having an outer sheath, the containment vessel comprising:
   a hollow element having a wall, a proximal end, a distal end, and a lumen extending between the proximal end and the distal end, the lumen of the hollow element being configured and adapted to contain a medical implant in a partially-deployed configuration during storage and sterilizing of the medical implant; and
   a proximal end cap including a secondary proximal end cap removably secured thereto and configured to reversibly seal the proximal end cap to the outer sheath, whereupon a closed fluid connection is established between the lumen of the hollow element and a lumen of the outer sheath;
   wherein the proximal end cap includes a sheathing guide configured and adapted to compress and to direct the medical implant into the lumen of the outer sheath.

2. The containment vessel of claim 1, wherein the medical implant is stored within the lumen of the hollow element in a wet condition.

3. The containment vessel of claim 1, wherein the containment vessel for the medical implant includes a distal end cap having an outlet configured to selectively release storage fluid from within the lumen of the hollow element.

4. The containment vessel of claim 3, wherein the storage fluid includes one or more biocidal fluids.

5. The containment vessel of claim 3, wherein the distal end cap includes an outlet configured to selectively release rinsing fluid from within the lumen of the hollow element.

6. The containment vessel of claim 1, wherein the sheathing guide is integrally formed with the proximal end cap.

7. The containment vessel of claim 1, wherein the containment vessel includes a radiopaque sleeve disposed about the lumen of the hollow element.

8. The containment vessel of claim 7, wherein the radiopaque sleeve is disposed about the wall of the hollow element.

9. The containment vessel of claim 7, wherein the radiopaque sleeve is configured to limit exposure of the medical implant to 4 gray or less of ionizing radiation when the medical implant is stored in the lumen of the hollow element and the containment vessel is exposed to 15 gray or more of ionizing radiation.

10. The containment vessel of claim 1, wherein the proximal end cap is threadably secured to the proximal end of the hollow element.

11. The containment vessel of claim 1, wherein the medical implant is a replacement heart valve.

12. The containment vessel of claim 1, wherein the secondary proximal end cap is threadably secured to the proximal end cap.

13. The containment vessel of claim 12, wherein the proximal end cap includes a sealing element disposed therein, the secondary proximal end cap being configured to compress the sealing element against an outer surface of the outer sheath.

14. The containment vessel of claim 1, wherein the proximal end cap includes a sheath receiving portion configured to matingly abut a distal end of the outer sheath.

15. The containment vessel of claim 1, wherein the sheathing guide includes a tapered surface extending from a distal end of the sheathing guide toward a proximal end of the proximal end cap.

16. The containment vessel of claim 15, wherein the tapered surface tapers radially inwardly from the distal end of the sheathing guide toward the proximal end of the proximal end cap.

17. The containment vessel of claim 1, wherein a minimum inner diameter of the sheathing guide is less than an inner diameter of the lumen of the outer sheath at the distal end of the lumen of the outer sheath.

18. An accessory sheathing guide, comprising:
   a first portion and a second portion configured to matingly engage with the first portion to define a tapered surface tapering radially inwardly from a distal end of the accessory sheathing guide toward a proximal end of the sheathing guide,
   wherein the first portion is coupled to the second portion.

19. The accessory sheathing guide of claim 18, wherein the first portion is pivotably connected to the second portion by a hinge element.

20. An accessory sheathing guide, comprising:
   a first portion and a second portion configured to matingly engage with the first portion to define a tapered inner surface tapering from a maximum inner diameter adjacent a distal end of the accessory sheathing guide to a minimum inner diameter adjacent a proximal end of the sheathing guide,
   wherein
   the first portion is reversibly coupled to the second portion;
   wherein the first portion is separable from and independent of the second portion.

* * * * *